(12) United States Patent
Tass

(10) Patent No.: US 8,463,378 B2
(45) Date of Patent: Jun. 11, 2013

(54) DEVICE AND METHOD FOR CONDITIONED DESYNCHRONIZING STIMULATION

(75) Inventor: Peter Tass, Munich (DE)

(73) Assignee: Forschungszentrum Juelich GmbH, Juelich (DE)

(*) Notice: Subject to any disclaimer, the term of this patent is extended or adjusted under 35 U.S.C. 154(b) by 132 days.

(21) Appl. No.: 13/124,571

(22) PCT Filed: Oct. 16, 2009

(86) PCT No.: PCT/EP2009/007452
§ 371 (c)(1),
(2), (4) Date: Apr. 15, 2011

(87) PCT Pub. No.: WO2010/043413
PCT Pub. Date: Apr. 22, 2010

(65) Prior Publication Data
US 2011/0201977 A1    Aug. 18, 2011

(30) Foreign Application Priority Data
Oct. 17, 2008  (DE) .......................... 10 2008 052 078

(51) Int. Cl.
*A61H 1/00* (2006.01)
(52) U.S. Cl.
USPC .............................................................. 607/3
(58) Field of Classification Search
None
See application file for complete search history.

(56) References Cited

U.S. PATENT DOCUMENTS

| | | | |
|---|---|---|---|
| 2006/0020291 A1 | 1/2006 | Gozani et al. | |
| 2006/0047324 A1 | 3/2006 | Tass | |
| 2008/0046025 A1 | 2/2008 | Tass | |
| 2009/0105785 A1* | 4/2009 | Wei et al. | 607/48 |

FOREIGN PATENT DOCUMENTS

| | | |
|---|---|---|
| DE | 102 33 960 A1 | 2/2004 |
| DE | 10 2004 060 514 A1 | 6/2006 |
| EP | 1 145 735 A2 | 10/2001 |
| EP | 1 944 059 A2 | 7/2008 |

\* cited by examiner

*Primary Examiner* — Carl H Layno
*Assistant Examiner* — Paula J Stice
(74) *Attorney, Agent, or Firm* — Dickstein Shapiro LLP (57) ABSTRACT

A device having a first stimulation unit that generates electrical first stimuli suppressing a pathological synchronous activity of neurons in the brain and/or spinal cord of a patient upon administering the same to the brain and/or spinal cord of the patient, a second stimulation unit that generates optical and/or acoustic and/or tactile and/or vibratory second stimuli, and a controller that controls the first and the second stimulation units. The generation of the first and second stimuli optionally occurs in a first or in a second operating mode, and the controller actuates the first and the second stimulation units such that in the first operating mode the generation of at least 60% of the second stimuli is chronologically coupled to the generation of the first stimuli, and in the second operating mode the generation of at least 60% of the second stimuli is carried out without generating the first stimuli.

26 Claims, 9 Drawing Sheets

DEVICE AND METHOD FOR CONDITIONED DESYNCHRONIZING STIMULATION

CROSS REFERENCE TO RELATED APPLICATIONS

This application is a National Stage of PCT/EP2009/007452, filed on Oct. 16, 2009, which claims the benefit of German Application No. 10 2008 052 078.0, filed on Oct. 17, 2008, all of which are incorporated by reference herein.

BACKGROUND

In the case of patients with neurological or psychiatric diseases, e.g. Parkinson's disease, essential tremor, dystonia, obsessive disorders, nerve cell networks exhibit pathological (abnormal) activity, e.g. excessively synchronous activity, in circumscribed regions of the brain, e.g. in the thalamus and the basal ganglia. In this case, a large number of neurons synchronously form action potentials, i.e. the involved neurons fire excessively synchronously. By contrast, in healthy individuals the neurons fire in a qualitatively different fashion in these regions of the brain, e.g. in an uncorrelated fashion.

In the case of Parkinson's disease, the pathologically (abnormally) synchronous activity changes the neuronal activity in other regions of the brain, e.g. in areas of the cerebral cortex such as the primary motor cortex. Here, the pathologically synchronous activity in the region of the thalamus and the basal ganglia impresses its rhythm onto the areas of e.g. the cerebral cortex, and so, ultimately, the muscles controlled by these areas develop a pathological activity, for example rhythmic trembling (tremor).

Neurological and psychiatric diseases with excessively pronounced neuronal synchronization are currently treated by electrical brain stimulation if medicinal therapy fails.

SUMMARY

A device having a first stimulation unit that generates electrical first stimuli suppressing a pathological synchronous activity of neurons in the brain and/or spinal cord of a patient upon administering the same to the brain and/or spinal cord of the patient, a second stimulation unit that generates optical and/or acoustic and/or tactile and/or vibratory second stimuli, and a controller that controls the first and the second stimulation units. The generation of the first and second stimuli optionally occurs in a first or in a second operating mode, and the controller actuates the first and the second stimulation units such that in the first operating mode the generation of at least 60% of the second stimuli is chronologically coupled to the generation of the first stimuli, and in the second operating mode the generation of at least 60% of the second stimuli is carried out without generating the first stimuli.

BRIEF DESCRIPTION OF THE DRAWINGS

In the following text, the system and method will be explained in more detail in an exemplary fashion with the aid of the drawings, in which.

DETAILED DESCRIPTION

Figure 1:
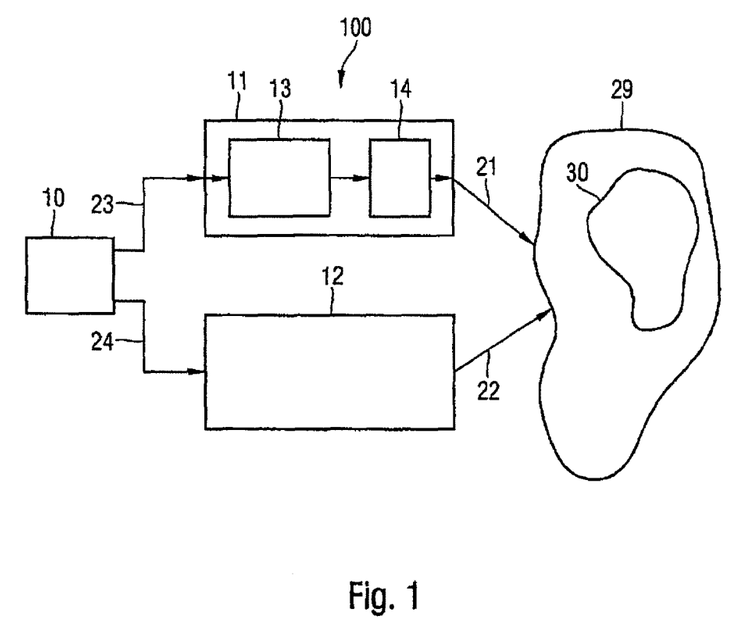
FIG. 1 shows a schematic illustration of a device 100 for conditioned desynchronizing stimulation as per an exemplary embodiment, during operation.

FIG. 1 schematically illustrates a device 100 for conditioned desynchronizing stimulation. The device 100 consists of a control unit 10, a first stimulation unit 11 and a second stimulation unit 12. The first stimulation unit 11 produces electrical first stimuli 21 and the second stimulation unit produces sensory second stimuli 22. The sensory second stimuli 22 are one or more stimuli from the group of optical stimuli, acoustic stimuli, tactile stimuli and vibration stimuli. The control unit 10 serves to control the two stimulation units 11 and 12 by means of control signals 23 and 24.

The device 100 can in particular be used for the treatment of neurological or psychiatric diseases, e.g. Parkinson's disease, essential tremor, dystonia, epilepsy, tremor as a result of multiple sclerosis or other pathological tremor, depression, motor disturbance, cerebellar diseases, obsessive disorders, Tourette's syndrome, functional disorders after a stroke, spasticity, tinnitus, sleep disorders, schizophrenia, substance dependencies, personality disorders, attention-deficit disorder, attention-deficit hyperactivity disorder, pathological gambling, neuroses, bulimia, burnout syndrome, fibromyalgia, migraine, cluster headache, general headache, neuralgia, ataxia, tic disorder or hypertonia, but also for the treatment of other diseases.

The aforementioned diseases can be caused by a disorder in the bioelectric communication of neural networks, which are connected in specific circuits. Herein, a neuron population continuously generates abnormal (pathological) neuronal activity and possibly an abnormal connectivity (network structure) associated therewith. In the process, a large number of neurons form action potentials at the same time, i.e. the involved neurons fire in an overly synchronous fashion. Additionally, the sick neuron population exhibits an oscillatory neuronal activity, i.e. the neurons fire rhythmically. In the case of neurological or psychiatric diseases, the average frequency of the abnormal (pathological) rhythmic activity of the affected neural networks lies approximately in the region of 1 to 30 Hz, but it can also lie outside of this range. By contrast, the neurons fire qualitatively differently in healthy humans, e.g. in an uncorrelated fashion.

In FIG. 1, the device 100 is illustrated in its intended operational state. During operation, the electrical first stimuli 21 are applied to the brain 29 and/or spinal cord 29 of a patient. At least one neuron population 30 in the brain 29 or spinal cord 29 of the patient has an pathologically synchronized neuronal activity as described above. In order to produce and apply the first stimuli 21, the first stimulation unit 10 can contain a generator unit 13 and at least one stimulation electrode 14. The generator unit 13 produces the first stimuli 21, which are transmitted to the stimulation electrode 14 by means of suitable connection lines. The stimulation electrode 14 has been placed into the brain 29 or into the region of the spinal cord 29 of the patient by surgery such that the first stimuli 21 are administered to the pathologically active neuron population 30, or at least to regions of the brain 29 or spinal cord 29 from where the first stimuli 21 are transmitted to the pathologically active neuron population 30 via the nervous system. The first stimuli 21 are embodied such that they suppress the pathologically synchronous activity of the neuron population 30 or even lead to a desynchronization of the neuron population 30. Since the first stimuli 21 are therapeutically effective electrical stimuli, they are also referred to as "specific" stimuli.

The second stimulation unit 12 produces optical, acoustic, tactile and/or vibratory second stimuli 22. The optical and/or acoustic second stimuli 22 are taken in by the eyes and ears, respectively, of the patient and are transmitted to the nervous system. The tactile second stimuli 22 can be pressure and/or touch stimuli, which are recorded by receptors situated in the skin of the patient. More particularly, these receptors include Merkel cells and Ruffini endings, which act as pressure receptors and, more particularly, as intensity detectors, and also Meissner's corpuscles and hair follicle receptors, which act as touch sensors and, more particularly, as velocity detectors. In contrast to the tactile second stimuli 22 relating to the surface sensitivity of the skin, the vibratory second stimuli 22 are predominately directed at the depth sensitivity. The vibratory second stimuli 22 can be recorded by receptors situated in the skin, the muscles, the subcutaneous tissue and/or the tendons of the patient. Pacinian corpuscles are mentioned in an exemplary fashion as receptors for the vibratory second stimuli 22; they impart vibration sensations and accelerations.

The second stimuli 22 can be consciously perceived by the patient and, more particularly, are not unpleasant for the patient. Applied on their own (i.e. without the interaction with the first stimuli 21 in the learning phase, as described below), the sensory second stimuli 22 do not have, or hardly have, a desynchronizing effect or a coincidence-rate-decreasing effect on the abnormally (pathologically) synchronous neuronal activity of the neuron population 30. The second stimuli 22 applied by the second stimulation unit 12 are therefore also referred to as "non-specific" stimuli.

In order to apply the first and second stimuli 21 and 22, the device 100 can be operated in two different modes of operation. By way of example, the respective mode of operation can be prescribed or can be selected by the control unit 10. The control unit 10 actuates the two stimulation units 11 and 12 in accordance with the selected mode of operation.

In a first mode of operation, which is also referred to as a learning phase, the non-specific second stimuli 22 are at least partly administered to the patient such that they are coupled closely in time to the application of the specific first stimuli 21, i.e. the first and second stimuli 21 and 22 are at least partly administered in pairs in the first mode of operation. This conditions the nervous system of the patient, i.e. said nervous system learns to react to the non-specific second stimuli 22 as it does to the specific first stimuli 21, even if the specific first stimuli 21 are not being applied. This is exploited by virtue of the fact that in the second mode of operation, which is the actual stimulation phase, the first and second stimuli 21 and 22 are not always administered in pairs; rather, non-specific second stimuli 22 are also applied on their own between such pairs of first and second stimuli 21 and 22. Since the second stimuli 22 also achieve therapeutic effects as a result of the conditioning of the nervous system of the patient achieved in the first mode of operation, i.e. in the learning phase, the necessary current input into the tissue of the patient required for the therapy is lowered in the second mode of operation, i.e. in the actual stimulation phase. Compared to conventional electrical brain stimulation, the current input can be reduced by e.g. up to a factor of 10 or more by means of the device 100.

An advantage of the significantly reduced current input is that there is a significant reduction in the probability of side effects occurring. This is because as the amount of applied stimulation current increases, there is an increase in the probability of stimulating not only the target area but also adjoining areas as well. This leads to a number of side effects, which are known to a person skilled in the art and in part are very unpleasant for the patient.

A further advantage of the reduced current input over a conventional stimulation method is that the reduced current input for stimulation purposes goes hand in hand with significantly reduced energy requirements of the generator unit, which is usually implanted into the patient. Since the dimensions of the battery decisively determine the dimensions of the generator unit, this allows the design of a smaller generator unit. The patient is much more comfortable with this, inter alia for cosmetic reasons. Moreover, there is a reduced risk of infection in the generator pouch, which correlates with the dimensions of the generator unit. Depending on the dimensions of the generator unit, the risk of infection in currently utilized generator units is approximately 5%; that is to say approximately 5% of patients develop an infection in the generator pouch, i.e. the tissue surrounding the generator unit, after the generator unit was implanted. As a result of the significant reduction in the current input, the generator dimensions can ultimately be e.g. minimized such that the entire generator unit can be placed into the hole drilled into the cranial bones.

Figure 2A:
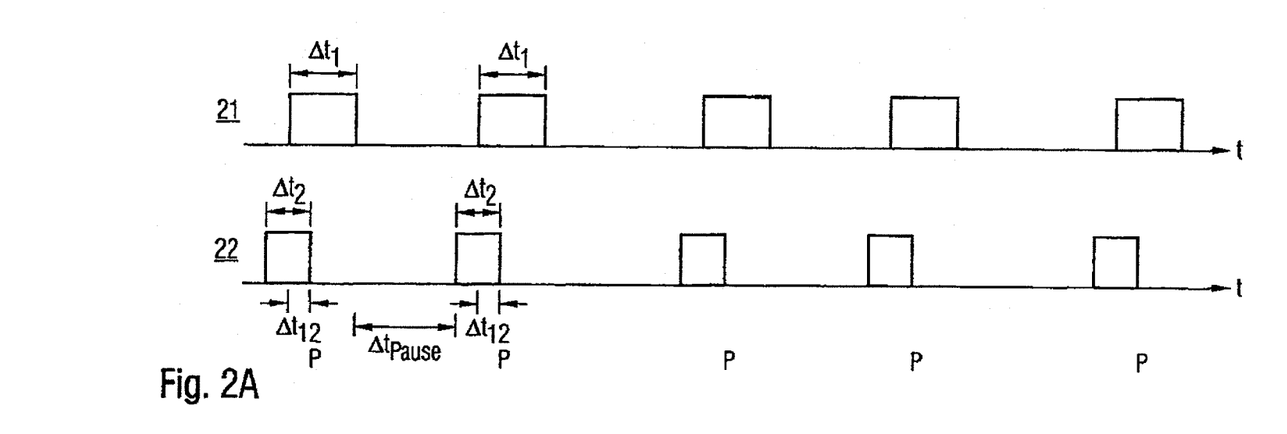
FIGS. 2A and 2B show schematic illustrations of two different modes of operation of the device 100.
Figure 2B:
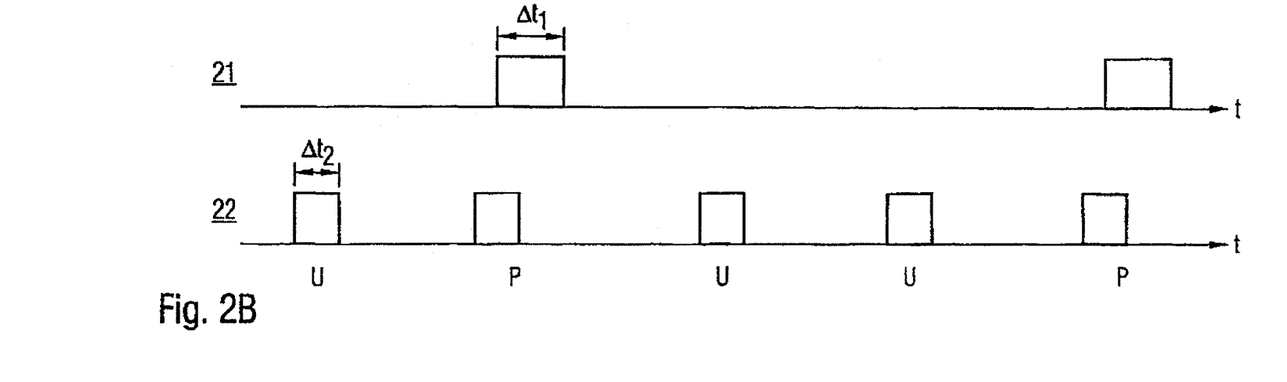

FIGS. 2A and 2B illustrate, in the form of a graph and in an exemplary fashion, the differences in the application of the first and second stimuli 21 and 22 in the first and the second mode of operation. In FIG. 2A, first time intervals $\Delta t_1$ and second time intervals $\Delta t_2$ are plotted, one above the other, against time t, during which time intervals the first stimuli 21 and the second stimuli 22 are generated and administered to the patient in the first mode of operation. The time intervals $\Delta t_1$ and $\Delta t_2$ are respectively represented by rectangles. FIG. 2A shows that, in the first mode of operation, the production and application of the non-specific second stimuli 22 is coupled to the production and application of the specific first stimuli 21. The time intervals $\Delta t_1$ and $\Delta t_2$ occur in pairs during the learning phase. As a result of the paired application of the stimuli 21 and 22, the brain 29 and/or spinal cord 29 of the patient is conditioned, i.e. once the learning phase has passed (e.g. already after two or more paired time intervals $\Delta t_1$ and $\Delta t_2$), even a non-specific second stimulus 22, which is applied without an additional specific first stimulus 21, causes a therapeutic effect like a specific first stimulus 21. Prior to this learning phase, a non-specific second stimulus 22 would not have caused a therapeutic effect.

The duration of the time intervals $\Delta t_1$, during which the specific first stimuli 21 are applied, lies e.g. between 30 minutes and 6 hours, but it can also lie outside of this range. The duration of the time intervals $\Delta t_2$, during which the non-specific second stimuli 22 are applied, lies e.g. between 10 minutes and 6 hours, but it can also lie outside of this range. By way of example, the time intervals $\Delta t_1$ overlap with the respectively associated time intervals $\Delta t_2$ in the first mode of operation. This overlap $\Delta t_{12}$ equals e.g. at least 10% or 20% or 30% or 40% or 50% or 60% or 70% or 80% or at least 90% or even 100% of the respective time interval $\Delta t_2$. In the case of time intervals $\Delta t_1$ and $\Delta t_2$, which are associated with one another, the time interval $\Delta t_2$ can start first, as illustrated in FIG. 2A; however, alternatively, the time interval $\Delta t_1$ can also start first. There are pauses between successive pairs of first and second stimuli 21 and 22, the length of which pauses $\Delta t_{Pause}$ can lie e.g. between 3 hours and 24 hours. The lengths of the time intervals $\Delta t_1$ and $\Delta t_2$ and the overlap periods $\Delta t_{12}$, and also the stimulation pauses $\Delta t_{Pause}$ can be varied during a stimulation phase. The duration of the learning phase, i.e. the time during which the device is operated in the first mode of operation, can be prescribed and can, for example, comprise a prescribed number of paired time intervals $\Delta t_1$ and $\Delta t_2$.

The following text describes examples of the application of the first and second stimuli 21 and 22 during the learning phase. According to one example, the first stimuli 21 and second stimuli 22 can be applied for a time interval $\Delta t_1$ of 6 hours and a time interval $\Delta t_2$ of 6.25 hours, respectively, with the time interval $\Delta t_2$ starting 15 minutes before the time interval $\Delta t_1$, and both time intervals $\Delta t_1$ and $\Delta t_2$ therefore end at the same time. This process could be repeated after a pause $\Delta t_{Pause}$ of e.g. 6 hours. In order to achieve rapid learning or conditioning of the nervous system, the number of learning events, i.e. the paired administration of first and second stimuli 21 and 22, could be increased further compared to the preceding example. Thus, the time intervals $\Delta t_1$ and $\Delta t_2$ could be reduced e.g. to 3 and 3.125 hours respectively, with the time interval $\Delta t_2$ starting 7.5 minutes before the time interval $\Delta t_1$. The coupled stimulation could be carried out again after a pause $\Delta t_{Pause}$ of e.g. 3 hours.

A learning effect can possibly already set in after two applications of first and second stimuli 21 and 22 coupled together. In order to design a conditioning of the nervous system that is as robust as possible and be able to use the conditioning for as long as possible during the actual stimulation phase, it is possible to carry out e.g. 10 to 50 pair applications during the learning phase, i.e. during the first mode of operation.

During the learning phase, it is not necessary for each time interval $\Delta t_2$ to be associated with a time interval $\Delta t_1$. By way of example, a time interval $\Delta t_1$ or $\Delta t_2$ can be inserted after a certain number of coupled-together time intervals $\Delta t_1$ and $\Delta t_2$, which inserted time interval is not coupled to an associated time interval $\Delta t_2$ or $\Delta t_1$ and during which merely first stimuli 21 or second stimuli 22 are produced and applied. By way of example, at least 50% or 60% or 70% or 80% or 90% or even 100% of time intervals $\Delta t_2$ can be coupled to an associated time interval $\Delta t_1$ in the first mode of operation. Furthermore, at least 50% or 60% or 70% or 80% or 90% or even 100% of time intervals $\Delta t_1$ can be coupled to an associated time interval $\Delta t_2$ in the first mode of operation.

The actual stimulation phase follows the learning phase carried out in the first mode of operation. To this end, the control unit 10 switches into the second mode of operation. FIG. 2B plots, one above the other and in an exemplary fashion, the time intervals $\Delta t_1$ and $\Delta t_2$ over time t, during which time intervals the first stimuli 21 or the second stimuli 22 are produced and applied in the second mode of operation.

During the actual stimulation phase, use is made of the fact that non-specific second stimuli 22 also have a therapeutic effect as a result of the conditioning of the nervous system of the patient achieved during the learning phase. To this end, unlike the learning phase, it is not predominately pairs consisting of first and second stimuli 21 and 22 that are applied; rather, it is only second stimuli 22 that are also repeatedly applied during a time interval $\Delta t_2$, which second stimuli are not coupled to the application of a first stimulus 21. By way of example, at least 10% or 20% or 30% or 40% or 50% or 60% or 70% or 80% or 90% of the time intervals $\Delta t_2$ are not associated with a time interval $\Delta t_1$ in the second mode of operation, i.e., overall, the number of time intervals $\Delta t_1$ in the second mode of operation is lower than the number of second time intervals $\Delta t_2$. According to one embodiment, time intervals $\Delta t_1$ that are not coupled to a time interval $\Delta t_2$ can also, on occasion, be inserted during the second mode of operation. According to a further embodiment, provision can e.g. also be made for none of the time intervals $\Delta t_2$ to be associated with a time interval $\Delta t_1$ in the second mode of operation.

The pairs "P" consisting of specific and non-specific stimuli 21 and 22, and the individually applied non-specific stimuli "U" can be administered in e.g. periodic sequences during the second mode of operation, e.g. in the following sequence: P-P-U-U-U-P-P-U-U-U-P-P-U-U-U- . . . . The temporal pattern, according to which the non-specific second stimuli 22 occur alone, can however also be deterministic or stochastic or a deterministic-stochastic mixture; for example, the following sequence may be selected: P-P-U-U-U-P-P-U-U-U-U-U-P-P-U-U-U-P-P-U-U-P-P-U-U-U-U-U-P-P-U-U-U- . . . .

The stimulation effect achieved by means of the device 100 can for example be monitored with the aid of a measuring unit. A device 300 containing such a measuring unit 15 is illustrated schematically in FIG. 3. The remaining components of the device 300 are identical to the device 100 shown in FIG. 1. The measuring unit 15 records one or more measurement signals 25, measured on the patient; converts these measurement signals into electrical signals 26 where necessary; and transmits said signals to the control unit 10. In particular, the measuring unit 15 can measure the neuronal activity in the stimulated target area, i.e. e.g. the neuronal activity in the neuron population 30 illustrated schematically in FIG. 3, or it can measure the neuronal activity of an area connected to the neuron population 30.

Figure 3:
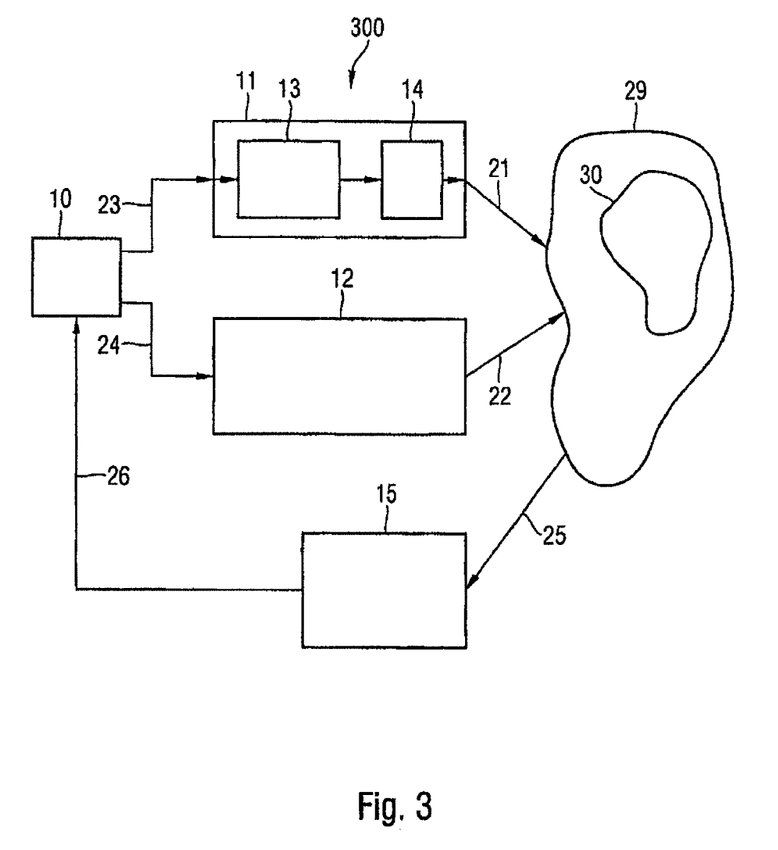
FIG. 3 shows a schematic illustration of a device 300 for conditioned desynchronizing stimulation as per a further exemplary embodiment, during operation.

The measuring unit 15 in the form of one or more sensors can be implanted into the body of the patient. By way of example, deep brain electrodes, subdural or epidural brain electrodes, subcutaneous EEG electrodes and subdural or epidural spinal cord electrodes can serve as invasive sensors. Moreover, electrodes to be attached to peripheral nerves can also be used as sensors. By way of example, the invasive sensor can be the same electrode 14 that is also used to apply the first stimuli 21.

The measurement signals 25 can be recorded in the pauses between the administration of the specific first stimuli 21, but more particularly also when only the non-specific second stimuli 22 are being administered. Provided that the neuronal activity of the target population 30 is measured, the amplitude of the pathological oscillations can be established in typical frequency ranges of the local field potentials, that is to say e.g. the integrated power in the beta-wave region of between 10 and 30 Hz in the case of akinetic patients with Parkinson's disease. This amplitude drops in the case of an effective stimulation. If the stimulation effect of the solely applied non-specific second stimuli 22 drops off during the second mode of operation and the measured amplitude exceeds a prescribed threshold, the next learning phase in the first mode of operation can take place. This can again be followed by the actual stimulation in the second mode of operation.

The medical practitioner can set an individual threshold for each patient. Alternatively, typical values can be selected as a default setting for the threshold, e.g. the mean value of the amplitude plus twice the standard deviation in regions of the frequency spectrum without frequency peaks and above e.g. 70 Hz.

In addition to the invasive sensors or as an alternative thereto, use can also be made of one or more non-invasive sensors such as electroencephalography (EEG) electrodes, magnetoencephalography (MEG) sensors and electromyography (EMG) electrodes. Furthermore, an accelerometer, for example, can measure the pathological oscillatory activity in the tremor frequency region or hypokinesia (in the sense of a reduction of overall movement). If a prescribed value of the tremor activity is exceeded or a value drops below a critical value of the mean hourly activity (outside of nighttime hours), this initiates e.g. the next learning phase in the first mode of operation.

It is also feasible to use two thresholds for controlling the two modes of operation. By way of example, two thresholds $A_L$ and $A_S$ can be prescribed and used for a comparison with the amplitude of the pathological neuronal activity in the neuron population 30, which amplitude was measured by the measuring unit 15. The threshold $A_L$ can be greater than the threshold $A_S$ and constitute the more approximate of the two thresholds. If the amplitude of the beta-wave activity exceeds the value $A_L$, a switch is carried out from the second mode of operation into the first mode of operation and a renewed learning phase is carried out.

Should the amplitude of the beta-wave activity exceed the more precise threshold $A_S$ during the second mode of operation, the device 300 remains in the actual stimulation phase rather than switching into the first mode of operation, but there is an increased application of pairs "P" of specific first stimuli 21 and non-specific second stimuli 22. By way of example, to this end, a subsequence only consisting of non-specific stimuli "U" (-U-U-U-U-U-) can be skipped, and a jump is made to the next section in the sequence that has pairs "P" of specific and non-specific stimuli 21 and 22. Provided that, for example, a certain percentage of the second stimuli 22 are specified to be applied together with first stimuli 21 in the second mode of operation, this percentage of pairs "P" can be increased by a certain percentage when the threshold $A_S$ is exceeded. By way of example, 30% of the second stimuli 22 are applied as pairs "P" together with first stimuli 21 in the second mode of operation. When the threshold $A_S$ is exceeded, this percentage can, for example, be increased by 20% to 50%. As soon as the amplitude of the beta-wave activity thereafter drops below a further prescribed threshold it is possible to return again to the e.g. 30% provided in the second mode of operation.

The transition from the second into the first mode of operation can also be controlled by the patient by means of an external patient programming instrument. That is to say the patient has the option of pushing a button on a small, handy external instrument if the therapy seems insufficient, i.e. if e.g. the tremor or hypokinesia are too pronounced. Following a predefined mode, the control unit 10 then switches into the first mode of operation from the second mode of operation, i.e. it switches back into a new learning phase. Here, the predefined mode means that this switch over into the first mode of operation is already initiated by the first push of the button by the patient. However, the device 100 or 300 can also be set up by a medical practitioner such that the switch over into the first mode of operation is only brought about after a button is pushed a few times in a predefined time interval, e.g. after the button was pushed 3 times in half an hour.

In order to monitor the therapy, the device 100 or 300 registers the number of times the button is pushed, and the times associated therewith. This information can be read by the medical practitioner by means of an external programming instrument intended for the medical practitioner.

Provision can furthermore be made for there to be a switch back into the first mode of operation, i.e. the learning phase, from the second mode of operation after a predefined period of time. This switching mode does not necessarily require therapy monitoring with the aid of the measuring unit 15, i.e. this switching mode can be implemented both in the device 100 and in the device 300.

In order to generate the non-specific second stimuli 22, the second stimulation unit 12 can contain e.g. a loudspeaker, a light source (or image source) and/or a vibrator. In general, the second stimuli 22 should be strong enough to be consciously perceived by the patient. However, they should not be perceived as e.g. unpleasantly strong or irritating or even distracting. By way of example, a buzzer sound, a humming sound or a melody are options for acoustic second stimuli 22 produced by the loudspeaker during the time intervals $\Delta t_2$. Provided that optical signals are intended to be used as second stimuli 22, these can be e.g. abstract or object-like, patterns, which either are static or change in time during the time intervals $\Delta t_2$, e.g. a flower blowing in the wind, a fish swimming in water, a flying bird, a rising sun, etc. Tactile stimuli or vibration stimuli can be vibrations at frequencies that can be perceived by the patient and are produced by a mechanical vibrator during the time intervals $\Delta t_2$. Perceptible vibration stimuli can have frequencies in the region of between 10 and 160 Hz or above, whereas tactile stimuli have significantly lower frequencies, which are e.g. lower than 1 Hz. Use can also be made of mixtures of tactile and vibratory stimuli. The tactile and/or vibratory stimuli can e.g. be selected for comfort by the patient him/herself. The vibrator can also be used to exert a light, pleasantly massaging effect on the skin of the patient during the time intervals $\Delta t_2$.

The non-specific second stimuli 22 can be continuously administered to the patient from the beginning to the end of a respective time interval $\Delta t_2$. Alternatively, there may also be pauses in the application during the time intervals $\Delta t_2$; by way of example, during the time intervals $\Delta t_2$, the second stimuli 22 can be administered during certain time intervals interspersed by application pauses. These time patterns can also be varied, e.g. stochastically or deterministically or in a mixed stochastic-deterministic fashion. Provision can be made for the second stimuli 22 to be applied over at least 60% or 70% or 80% or 90% of the duration of each time interval $\Delta t_2$.

Desynchronizing electrical stimulation signals, or electrical stimulation signals that at least reduce the coincidence rate of the pathological neurons, are used as specific first stimuli 21. The stimulation electrode 14, by means of which the first stimuli 21 are transmitted to the brain 29 or spinal cord 29 of the patient, can for example have one or two or more stimulation contact surfaces, which are in contact with the tissue of the brain 29 or spinal cord 29 after implantation and are used to apply the electrical first stimuli 21.

Figure 4:
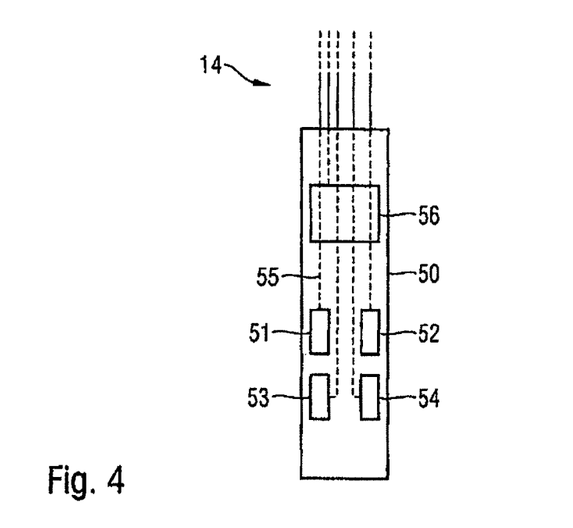
FIG. 4 shows a schematic illustration of an exemplary embodiment of a stimulation electrode 14.

FIG. 4 illustrates a stimulation electrode 14 in an exemplary and schematic fashion. The stimulation electrode 14 consists of an insulated electrode shaft 50 and at least one stimulation contact surface, for example two or more stimulation contact surfaces, which has/have been introduced into the electrode shaft 50. In the present example, the stimulation electrode 14 contains four stimulation contact surfaces 51, 52, 53 and 54. The electrode shaft 50 and the stimulation contact surfaces 51 to 54 can be made of a biocompatible material. Furthermore, the stimulation contact surfaces 51 to 54 are electrically conductive (e.g. they are produced from a metal) and are in direct electrical contact with the nerve tissue after implantation. In the present exemplary embodiment, each of the stimulation contact surfaces 51 to 54 can be actuated via its own lead 55, and the recorded measurement signals can be transported away via the leads 55. Alternatively, two or more stimulation contact surfaces 51 to 54 can also be connected to the same lead 55.

In FIG. 4, the stimulation contact surfaces 51 to 54 are arranged in rows and columns. Furthermore, the stimulation contact surfaces 51 to 54 are embodied as rectangles. These embodiments should merely be understood as being exemplary. As an alternative to these embodiments, the stimulation electrode 14 can contain any number N (N=1, 2, 3, 4, 5, 6, 7, 8, 9, 10, 11, 12, of stimulation contact surfaces, which can be arranged in an arbitrary fashion with respect to one another and can have arbitrary shapes.

In addition to the stimulation contact surfaces 51 to 54, the electrode 14 can have a reference electrode 56, the surface of which can be greater than those of the stimulation contact surfaces 51 to 54. The reference electrode 56 is used to produce a reference potential during the stimulation of the nerve tissue. Alternatively, one of the stimulation contact surfaces 51 to 54 can also be used for this purpose. That is to say there can be either unipolar stimulation between an individual stimulation contact surface 51 to 54 and the reference electrode 56 (or the housing of the generator unit 13) or bipolar stimulation between various stimulation contact surfaces 51 to 54.

In addition to its function as a stimulation electrode, the electrode 14 can also be used as a measuring unit 15 within the device 300. In this case, measurement signals are recorded by at least one of the contact surfaces 51 to 54.

The stimulation contact surfaces 51 to 54 can be connected to the generator unit 13 via cables or by telemetric connections.

The plurality of stimulation contact surfaces 51 to 54 allow separate stimulation of different regions of the brain 29 or spinal cord 29 by the individual stimulation contact surfaces 51 to 54. By way of example, each of the stimulation contact surfaces 51 to 54 can for this purpose be connected to the generator unit 13 by means of its own connection line 55. This allows the generator unit 13 to produce particular first stimuli 21 for each individual stimulation contact surface 51 to 54. The stimulation contact surfaces 51 to 54 can be implanted into the patient such that the first stimuli 21, which are applied to the tissue, are transmitted via nerves to different target areas situated in the brain 29 and/or spinal cord 29. It follows that the device 100 or 300 can stimulate different target areas in the brain 29 and/or spinal cord 29 with possibly different and/or time-offset first stimuli 21 during the same period of stimulation $\Delta t_1$.

The plurality of stimulation contact surfaces 51 to 54 afford the possibility of not only stimulating different regions of the brain 29 and/or spinal cord 29, but also of using other forms of stimulation than would be possible if e.g. only a single stimulation contact surface were used. According to one embodiment, the stimulation electrode 14 administers first stimuli 21 to the neuron population 30 with an pathologically synchronous and oscillatory activity, which stimuli bring about a resetting, a so-called reset, of the phase of the neuronal activity of the stimulated neurons in the neuron population 30. The reset sets the phase of the stimulated neurons to a certain phase value, e.g. 0°, independently of the current phase value. Hence the phase of the neuronal activity of the pathological neuron population 30 is controlled by means of a targeted stimulation. Furthermore, the plurality of stimulation contact surfaces 51 to 54 allow the stimulation of the pathological neuron population 30 at different sites. This affords the possibility of resetting the phase of the neuronal activity of the pathological neuron population 30 at different times at the different stimulation sites. As a result, this subdivides the pathological neuron population 30, the neurons of which were previously active in a synchronous fashion and with the same frequency and phase, into a plurality of subpopulations, which are illustrated schematically in FIG. 5 and are denoted by the reference signs 31, 32, 33, and 34. Within one of the subpopulations 31 to 34, the neurons are still synchronous and also still fire with the same pathological frequency after the phase has been reset, but each of the subpopulations 31 to 34 has the phase in respect of its neuronal activity that was imposed on it by the stimulation stimulus. This means that after the resetting of their phases, the neuronal activities of the individual subpopulations 31 to 34 still have an approximately sinusoidal profile with the same pathological frequency, but have different phases.

Figure 5:
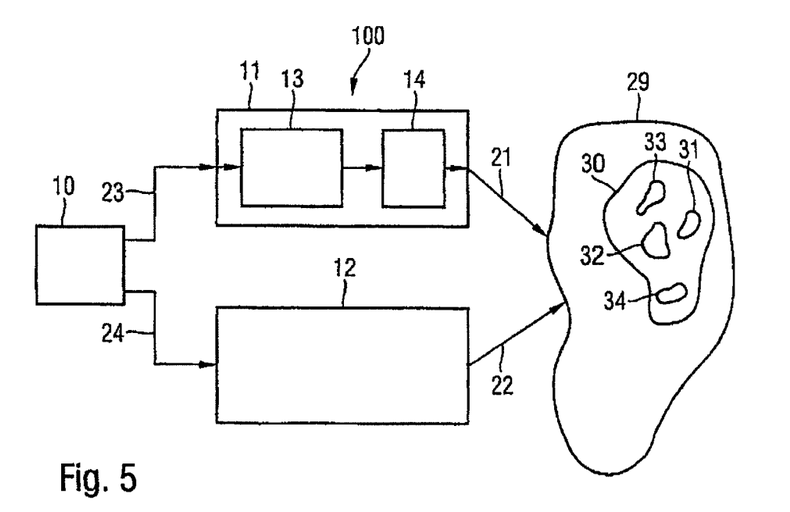
FIG. 5 shows a schematic illustration of the device 100 with the stimulation electrode 14, during operation.

By way of example, the stimulation contact surfaces 51 to 54 can be placed onto or in the brain tissue or spinal-cord tissue 29 of the patient such that the first stimuli 21 applied by the stimulation contact surface 51 stimulate the subpopulation 31 and reset the neuronal phase thereof, and the first stimuli 21 applied by the stimulation contact surface 52 stimulate the subpopulation 52 and reset the neuronal phase thereof. The same holds true for the stimulation contact surfaces 53 and 54 with respect to the subpopulations 33 and 34.

Due to the pathological interaction between the neurons, the state with at least two subpopulations, which state was generated by the stimulation, is unstable and the entire neuron population 30 quickly approaches a state of complete desynchronization, in which the neurons fire in an uncorrelated fashion. The desired state, i.e. the complete desynchronization, thus is not available immediately after the application of the stimulation signals via the stimulation electrode 14, but usually sets in within a few periods or even within less than one period of the pathological activity.

A theory for explaining the stimulation success is based on the fact that the ultimately desired desynchronization is only made possible by the pathologically increased interaction between the neurons. Hereby, a self-organization process is utilized, which is responsible for the pathological synchronization. The same process brings about a desynchronization following a subdivision of an entire population 30 into subpopulations 31 to 34 with different phases. In contrast to this, there would not be desynchronization without an pathologically increased interaction between the neurons.

Moreover, the electrical stimulation with the device 100 or 300 can obtain a restructuring of the connectivity of the dysfunctional neural networks and so long-lasting therapeutic effects can be brought about. The obtained synaptic reorganization is of great importance for the effective treatment of neurological or psychiatric disorders.

If differently embodied stimulation signals were used instead of the stimulation signals that can control the phases of the stimulated neurons, e.g. high-frequency, continuously applied high-frequency pulse trains, the above-described, long-lasting therapeutic effects could typically not be attained, and this would result in stimulation that requires continuous and comparatively high-current stimulation. In contrast to this, the stimulation forms described here only require little energy to be introduced into the neuron system from the outside in order to obtain a therapeutic effect. As a result of the relatively low energy input into the body of the patient and the often very quickly obtained stimulation results, the device 100 or 300 can significantly reduce dysesthesia and paresthesia (painful sensations) that often go hand in hand with an electrical nerve stimulation.

Different approaches can be taken for obtaining a desynchronization of the entire neuron population 30 as a result of time-offset resetting of the phases of the subpopulations 31 to 34 of the pathologically synchronous neuron population 30. By way of example, stimulation signals that bring about a reset in the phase of neurons can be emitted with time delay to the respectively stimulated nerve tissue by means of the various stimulation contact surfaces 51 to 54. Furthermore, the stimulation signals can be applied e.g. with phase offset or with different polarity, and so these also lead to a time-offset reset in the phases of the various subpopulations 31 to 34.

By way of example, the device 100 can be operated in a so-called "open loop" mode, in which the generator unit 13 produces predetermined first stimuli 21 and emits these to the nerve tissue by means of the stimulation contact surfaces 51 to 54. Moreover, the device 100 can also be developed to form the device 300 shown in FIG. 3, the latter device constituting a so-called "closed loop" system. The device 300 additionally contains the measuring unit 15, which provides one or more measurement signals 26 recorded in the patient and transmits said signals to the control unit 10.

The measurement signals 26 can be used to carry out demand-driven stimulation. To this end, the control unit 10 detects the presence and/or extent of one or more pathological features using the measurement signals 26 recorded by the measuring unit 15. By way of example, as already explained above, the amplitude or the magnitude of the neuronal activity can be measured, can be compared to one or more prescribed thresholds and a particular mode of operation can be selected, depending on the result of the comparison. The generator unit 13 can be embodied such that stimulation or the first mode of operation is started as soon as the prescribed threshold is exceeded. Furthermore, the measurement signals 26 recorded by the measuring unit 15 can be used to set e.g. the strength of the first stimuli 21. By way of example, one or more thresholds can be prescribed, and a certain strength of the first stimuli 21 is set when the amplitude or the magnitude of the measurement signals 26 exceeds a certain threshold.

Moreover, provision can be made for the measurement signals 26, recorded by the measuring unit 15, to be utilized directly or, if need be, after one or more processing steps as first stimuli 21 and for said signals to be transmitted to the stimulation electrode 14 by the generator unit 13. By way of example, the measurement signals 26 can be amplified and can be processed with a time delay and with linear and/or nonlinear calculation steps and combinations, optionally after mathematical calculations (e.g. after mixing the measurement signals), and can be transmitted to the stimulation electrode 14. Here, the calculation mode is selected such that the pathological neuronal activity is counteracted and the stimulation signal likewise disappears, or is at least significantly reduced in strength, with decreasing pathological neuronal activity.

Figure 6:
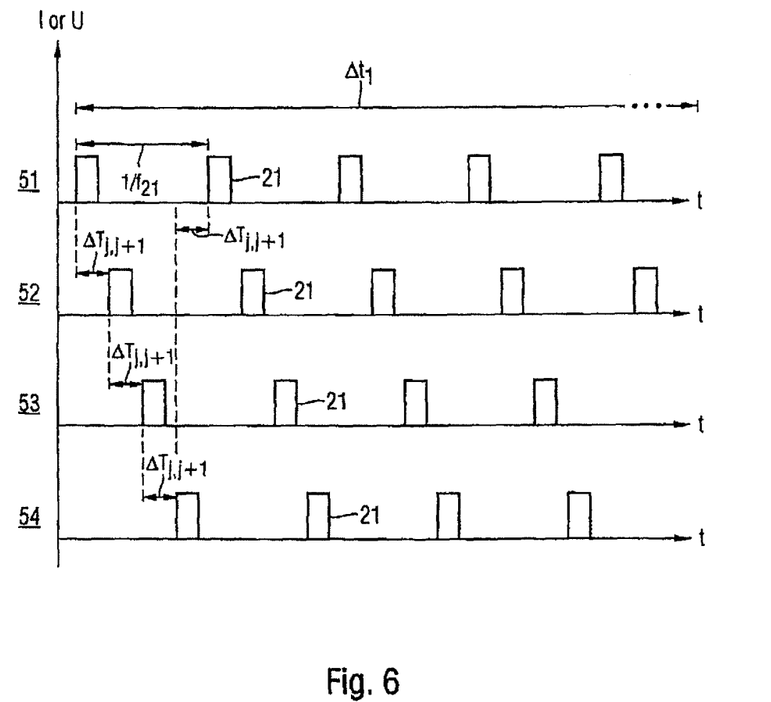
FIG. 6 shows a schematic illustration of specific electrical stimuli that are applied by means of a plurality of stimulation contact surfaces.

A stimulation method suitable for the above-described purposes, which can, for example, be carried out with one of the devices 100 and 300, is schematically illustrated in FIG. 6. There, the first stimuli 21 applied by the stimulation contact surfaces 51 to 54 are plotted, one above the other, against time t. The period of time shown in FIG. 6 constitutes an interval from a time interval $\Delta t_1$. The illustrated stimulation can be continued to the end of the time interval $\Delta t_1$.

In the method illustrated in FIG. 6, each of the stimulation contact surfaces 51 to 54 periodically administers the first stimulus 21 to the respective region of the tissue on which the stimulation contact surface 51 to 54 has been placed. The frequency $f_{21}$, at which the first stimuli 21 are repeated for each stimulation contact surface 51 to 54, can lie in the region of between 1 and 30 Hz and more particularly in the region of between 1 and 20 Hz or in the region of between 5 and 20 Hz or in the region of between 10 and 30 Hz, but it can also assume smaller or larger values.

According to the embodiment shown in FIG. 6, the first stimuli 21 are administered by the individual stimulation contact surfaces 51 to 54, with there being a time delay between the administrations by the individual stimulation contact surfaces 51 to 54. By way of example, the start of successive first stimuli 21, applied by different stimulation contact surfaces 51 to 54, can be shifted by a time $\Delta T_{j,j+1}$.

In the case of N stimulation contact surfaces, the time delay $\Delta T_{j,j+1}$ between two successive first stimuli 21 can for example lie in the region of an N-th of the period $1/f_{21}$. In the exemplary embodiment (N=4) shown in FIG. 6, the delay $\Delta T_{j,j+1}$ then is $1/(4 \times f_{21})$.

By way of example, the frequency $f_{21}$ can lie in the region of the mean frequency of the pathological rhythmic activity of the target network. In the case of neurological and psychiatric diseases, the mean frequency typically lies in the region of between 1 and 30 Hz, but it can also lie outside of this region. It should be noted here that the frequency at which the affected neurons fire synchronously in neurological and psychiatric diseases usually is not constant but can by all means have variations and, moreover, has individual deviations in each patient.

Figure 7:
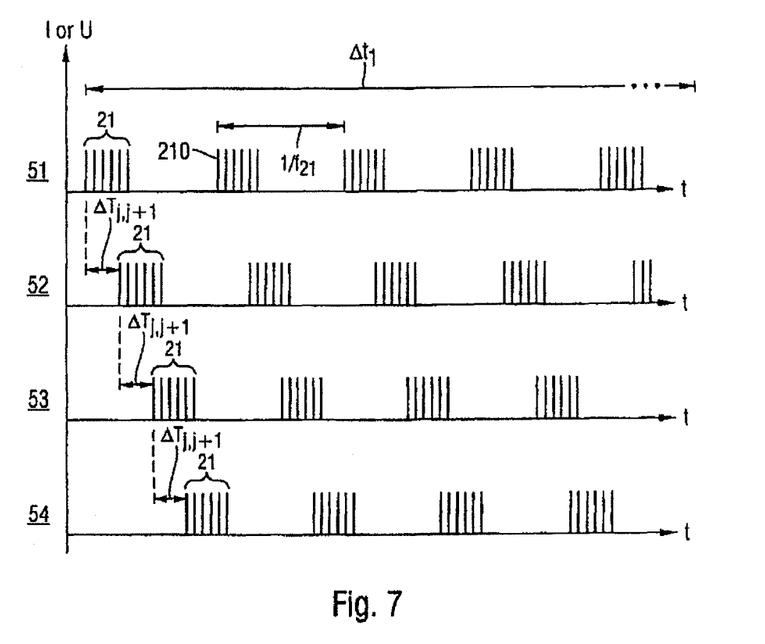
FIG. 7 shows a schematic illustration of sequences of electrical pulse trains, which are applied by means of a plurality of stimulation contact surfaces.

By way of example, current-controlled or voltage-controlled pulses can be used as first stimuli 21. Furthermore, a first stimulus 21 can be a pulse train consisting of a plurality of individual pulses 210, as illustrated in FIG. 7. The pulse trains 21 can each consist of 1 to 100, more particularly 2 to 10, electric-charge-balanced individual pulses 210. The pulse trains 21 are applied e.g. as sequence with up to 20 or more pulse trains. Within one sequence, the pulse trains 21 are repeated with the frequency $f_{21}$ in the region of 1 to 30 Hz.

Figure 8:
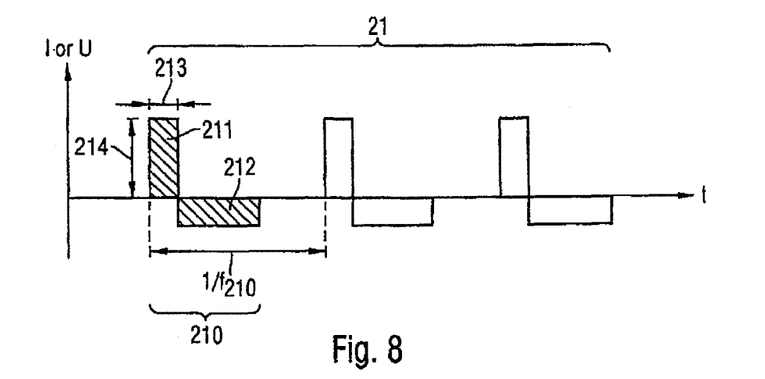
FIG. 8 shows a schematic illustration of an electrical pulse train.

FIG. 8 shows a pulse train 21, which consists of three individual pulses 210, in an exemplary fashion. The individual pulses 210 are repeated with a frequency $f_{210}$ in the region of 50 to 500 Hz, more particularly in the region of 100 to 150 Hz. The individual pulses 210 can be current-controlled or voltage-controlled pulses, which are composed of an initial pulse component 211 and a subsequent pulse component 212 flowing in the opposite direction, wherein the polarity of the two pulse components 211 and 212 can also be interchanged compared to the polarity shown in FIG. 8. The duration 213 of the pulse component 211 lies in the region of between 1 µs and 450 µs. The amplitude 214 of the pulse component 211 is in the region of between 0 mA and 25 mA in the case of current-controlled pulses and in the region of between 0 and 20 V in the case of voltage-controlled pulses.

The amplitude of the pulse component 212 is smaller than the amplitude 214 of the pulse component 211. Instead, the pulse component 212 has a longer duration than the pulse component 211. Ideally, the pulse components 211 and 212 are dimensioned such that the charge transmitted thereby has the same magnitude in both pulse components 211 and 212, i.e. the areas shaded in FIG. 8 have the same size. As a result, an individual pulse 210 introduces precisely the same amount of charge into the tissue as is removed from the tissue.

The rectangular shape of the individual pulses 210 illustrated in FIG. 8 constitutes an ideal shape. There are deviations from the ideal rectangular shape, which depend on the quality of the electronics producing the individual pulses 210.

Instead of pulse-shaped stimulation signals, the generator unit 13 can for example also produce differently embodied stimulation signals, e.g. stimulus patterns that are continuous in time. The above-described signal shapes and the parameters thereof should merely be understood as being exemplary. Provision can by all means be made for there to be deviations from the aforementioned signal shapes and the parameters thereof.

There can be various deviations from the strictly periodic stimulation pattern shown in FIG. 6. By way of example, the time delay $\Delta T_{j,j+1}$ between two successive first stimuli 21 need not necessarily always be of the same magnitude. Provision can by all means be made for the time separations between the individual first stimuli 21 to be selected such that they differ. Furthermore, the delay times can also be varied during the treatment of a patient. The delay times can also be adjusted in respect of the physiological signal run times.

Figure 9:
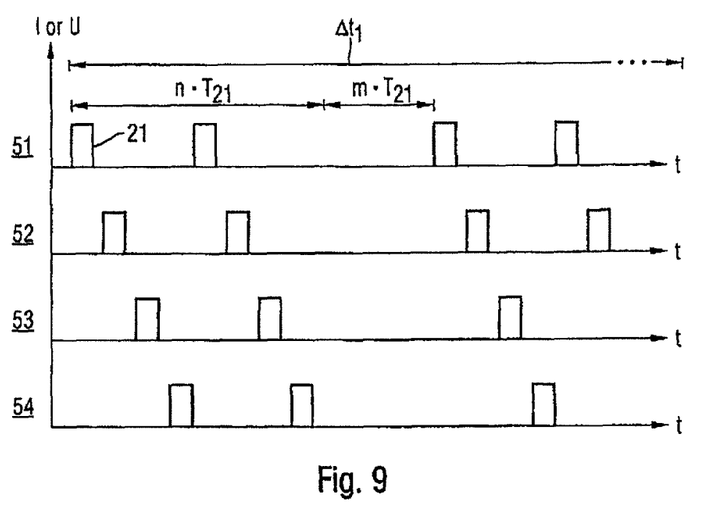
FIG. 9 shows a schematic illustration of a variation of the stimulation shown in FIG. 6.

Furthermore, pauses can be provided during the application of the first stimuli 21, during which pauses there is no stimulation. Such a pause is shown in an exemplary fashion in FIG. 9. The pauses can be selected to have any duration and more particularly be an integer multiple of the period $T_{21}$ ($=1/f_{21}$). Moreover, there can be a pause after any number of stimulations. By way of example, stimulation can be performed over n successive periods of length $T_{21}$, and there can subsequently be a pause without stimulation over m periods of length $T_{21}$, wherein n and m are small whole numbers, for example in the region of between 1 and 10. This scheme can be either continued periodically or modified stochastically and/or deterministically, e.g. chaotically.

A further option for deviating from the strictly periodic stimulation pattern shown in FIG. 6 consists of stochastic or deterministic or mixed stochastic-deterministic variation of the temporal sequence of the individual first stimuli 21.

Figure 10:
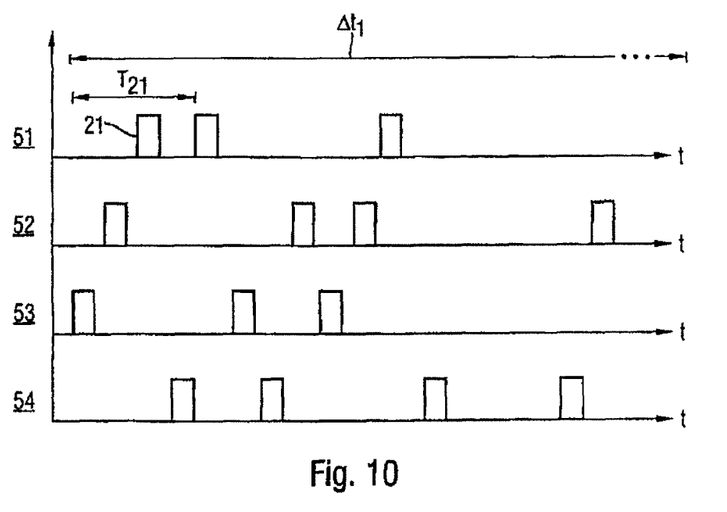
FIG. 10 shows a schematic illustration of a further variation of the stimulation shown in FIG. 6.

Additionally, the order in which the stimulation contact surfaces 51 to 54 apply the first stimuli 21 can be varied during each period $T_{21}$ (or else during other time steps), as illustrated in FIG. 10 in an exemplary fashion. This variation can be stochastic or deterministic or mixed stochastic-deterministic.

Furthermore, it is possible for only a certain number of stimulation contact surfaces 51 to 54 to be used for stimulation in each time interval $T_{21}$ (or in another time interval) and the stimulation contact surfaces involved in the stimulation can be varied in each time interval. This variation can also be stochastic or deterministic or mixed stochastic-deterministic.

All stimulation forms described above can also be performed in a "closed loop" mode by means of the device 300. With respect to the stimulation form shown in FIG. 9, the start time and the length of the pause can for example be selected as controlled by demand.

As already described above in conjunction with the device 300, the "closed loop" mode of the device 300 can be embodied such that the measurement signals 26 recorded by the measuring unit 15 are converted into electrical first stimuli 21 by the generator unit 13, either directly or, if need be, after one or more processing steps, and are applied by the stimulation electrode 14. In this case, the device 300 does not necessarily require at least two stimulation contact surfaces. This type of stimulation, in which the measurement signals recorded on the patient are transmitted back into the body of the patient, could, in principle, also be carried out with only a single stimulation contact surface; however, an arbitrary larger number of stimulation contact surfaces can also be provided.

The above-described "closed loop" mode can likewise be used for desynchronization of a neuron population with an pathologically synchronous and oscillatory neuronal activity.

By way of example, in order to produce the first stimuli 21, the measurement signals 26 can be amplified and can be used as first stimuli 21 for the electrical stimulation with a time delay and with linear and/or nonlinear calculation steps, optionally after mathematical calculations (e.g. after mixing the measurement signals). Here, the calculation mode can be selected such that the pathological neuronal activity is counteracted and the stimulation signal likewise disappears, or is at least significantly reduced in strength, with decreasing pathological neuronal activity.

In the following text, linear and nonlinear processing steps are described, which can be used to process the measurement signals 26 obtained with the aid of the measuring unit 15 before they are transmitted to the stimulation electrode 14.

In the case of nonlinear processing of the measurement signals 26, it is not the phase of the neuronal activity in the respective stimulated subpopulations that is reset, but the synchronization in the pathologically active neuron population is suppressed by influencing the saturation process of the synchronization.

In the case of linear processing of a measurement signal 26 obtained from the measuring unit 15, the measurement signal 26 can, for example, be filtered and/or amplified and/or be subjected to a time delay before the thus processed signal is transmitted to the stimulation electrode 14 and applied by the stimulation contact surface or surfaces. By way of example, the measurement signal 26 has been recorded by an EEG electrode and reproduces the pathological activity in the target area. Accordingly, the measurement signal 26 is a sinusoidal oscillation with a frequency in the region of between 1 and 30 Hz. By way of example, the measurement signal 26 furthermore has a frequency of 5 Hz. The measurement signal 26 can be filtered by a band-pass filter with a pass-band in the region of 5 Hz and can be amplified by an amplifier such that it has suitable levels for the electrical brain stimulation or spinal-cord stimulation. The amplified sinusoidal oscillation thus obtained is subsequently used to actuate the stimulation electrode 14.

Provided that a plurality of stimulation contact surfaces are used for the stimulation, the measurement signal 26 can be subjected to the time delays $\Delta T_{j,j+1}$, illustrated in FIG. 6, before it is transmitted to the corresponding stimulation contact surfaces as first stimulus 21. According to the preceding example, sinusoidal oscillations with a frequency of 5 Hz are applied instead of the rectangular stimulation signals 21 shown in FIG. 6.

With the aid of an example, the following text explains how a measurement signal 26 obtained by the measuring unit 15 can be subjected to nonlinear processing before it is used as a first stimulus 21 for electrical brain stimulation or spinal-cord stimulation. As in the case of linear processing, the measurement signal 26 can in this case also be filtered and/or amplified and/or be subjected to a time delay.

The start point is an equation for the stimulation signal S(t) (first stimulus):

$$S(t)=K \cdot \overline{Z}^2(t) \cdot \overline{Z}^*(t-\tau). \qquad (1)$$

In equation (1), K is an amplification factor that can be selected in a suitable fashion and $\overline{Z}(t)$ is an average state variable of the measurement signal. $\overline{Z}(t)$ is a complex variable and can be represented as follows:

$$\overline{Z}(t)=X(t)+iY(t),$$

wherein X(t) can correspond to e.g. the neurological measurement signal. Since the considered frequencies lie in the region of 10 Hz=1/100 ms=1/$T_\alpha$, the imaginary part Y(t) can be approximated by X(t−$\tau_\alpha$), wherein for example $\tau_\alpha$=$T_\alpha$/4 holds true. This results in:

$$S(t)=K\cdot[X(t)+iX(t-\tau_\alpha)]^2\cdot[X(t-\tau-\tau_\alpha)]. \quad (3)$$

Equation (3) can be rewritten as follows:

$$S(t)=K\cdot[X(t)^2\cdot X(t-\tau)+i2X(t)\cdot(t-\tau_\alpha)\cdot X(t-\tau)-X(t-\tau_\alpha)\cdot X(t-\tau)-iX(t-\tau-\tau_\alpha)\cdot X(t)^2+2X(t)\cdot X(t-\tau_\alpha)\cdot X(t-\tau-\tau_\alpha)+iX(t-\tau-\tau_\alpha)\cdot X(t-\tau_\alpha)]. \quad (4)$$

The real part of equation (4) is used as the stimulation signal:

$$\mathrm{real}[S(t)]=K\cdot[X(t)^2\cdot X(t-\tau)-X(t-\tau_\alpha)\cdot X(t-\tau)+2X(t)\cdot X(t-\tau_\alpha)\cdot X(t-\tau-\tau_\alpha)] \quad (5)$$

Figure 11:
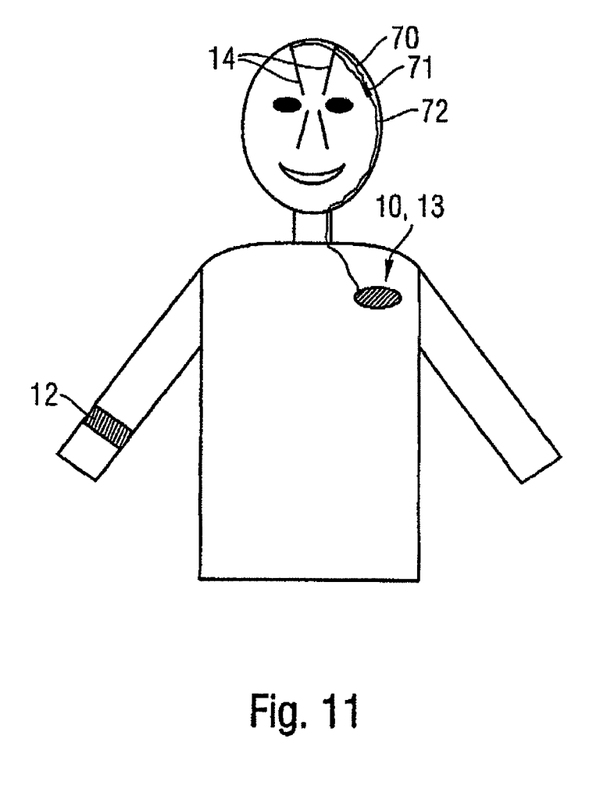
FIG. 11 shows a schematic illustration of the device 100 for conditioned desynchronizing stimulation as per an exemplary embodiment, during operation.

FIG. 11 schematically illustrates the device 100 or 300 during its intended operation. To this end, at least one stimulation electrode 14 has been implanted into one or both sides of the brain of a patient. The stimulation electrodes 14 placed into one or more of the aforementioned target areas are each connected to the generator unit 13 by a cable 70, via a connector 71 and a further-connecting cable 72. In the present embodiment, the generator unit 13 also comprises the control unit 10. The aforementioned components of the device 100 are implanted in the body of the patient. The connecting cables 70 and 72, and the connector 71, are implanted under the skin. As an alternative to a pectorally implanted generator unit 13, as illustrated in FIG. 11, a smaller generator can also be implanted directly into the drilled hole. This can reduce the infection rate in the generator pouch, and breaks in the connecting cables 70 and 72 can be avoided. Furthermore, a semi-implant with a radio link can be used instead of a full implant. In the case of a "closed loop" stimulation, the device 300 also contains a measuring unit 15. The second stimulation unit 12 for producing the non-specific second stimuli 22 is attached to the arm of the patient in the present example. The second stimulation unit 12 can communicate with the control unit 10 situated in the body of the patient by means of e.g. a radio link.

Figure 12A:
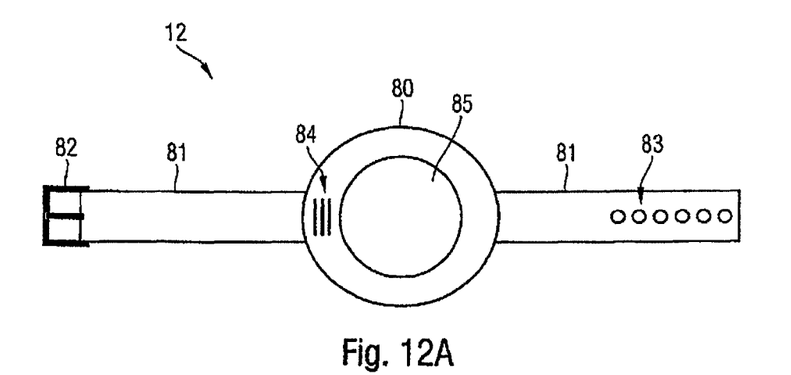
FIGS. 12A and 12B show schematic illustrations of an exemplary embodiment of a stimulation unit for producing and applying non-specific optical stimuli, acoustic stimuli, tactile stimuli and vibration stimuli.
Figure 12B:
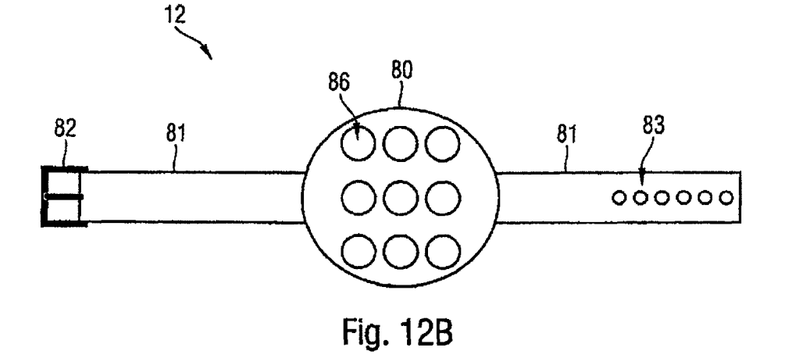

FIGS. 12A and 12B illustrate an exemplary embodiment of the second stimulation unit 12 for producing the non-specific second stimuli 22. In the present case, the second stimulation unit 12 is embodied as a so-called "conditioning watch", which the patient can wear comfortably. FIG. 12A shows the front view; FIG. 12B shows the rear view of the conditioning watch 12. The conditioning watch 12 consists of a central part 80, straps 81, a fastener part 82 and associated holes 83. Alternatively, use can also be made of a hook-and-loop fastener or any other equivalent fastener. The central part 80 contains a loudspeaker 84 for generating non-specific acoustic signals 22, e.g. a melody or a pleasant buzzer sound, and also a display 85 for generating a pleasant, non-blinding non-specific optical stimulus 22, e.g. a flower blowing in the wind or an abstract light pattern with bright and warm colors. Furthermore, the conditioning watch 12 can be equipped with one or more vibrators 86, which generate non-specific tactile and/or vibratory stimuli 22. In order to produce tactile stimuli 22, the vibrators can be operated at frequencies of less than 1 Hz. More particularly, the moveable parts of the vibrators 86 can in this case be aligned such that they can implement pressure stimuli in an improved fashion, i.e. the main movement direction of the vibrators 86 should be directed into the skin. Furthermore, the tactile stimuli 22 could also be produced by pressure actuators or elements that move slowly relative to the skin, which elements can for example be integrated into the conditioning watch. Provided that vibratory stimuli 22 should be produced by means of the vibrators 86, vibration frequencies in the region of between 10 and 160 Hz or above can be implemented. In this case, the moveable parts of the vibrators 86 can have a pronounced movement direction substantially parallel to the skin. The vibrators 86 can also be operated such that they produce tactile and vibratory stimuli 22 at the same time.

The conditioning watch 12 can also be embodied such that it only generates a non-specific stimulus 22 for one of the senses, e.g. only an optical stimulus. The conditioning watch 12 is supplied with current by a battery and/or solar cells and/or a mechanical flywheel in the interior of the conditioning watch 12.

In order to monitor the stimulation effect, the conditioning watch 12 can additionally contain an accelerometer, which can measure the pathological oscillatory activity, e.g. from an pathological tremor, or else the mean activity level of the patient. The mean activity level of the patient reflects the slowing down or dropping off of the movement of the patient or the inability of the patient to move (i.e. bradykinesia, hypokinesia, and akinesia).

Figure 13:
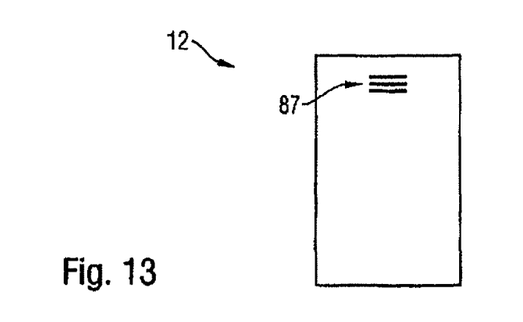
FIG. 13 shows a schematic illustration of a further exemplary embodiment of a stimulation unit for producing and applying acoustic stimuli.

A further exemplary embodiment of the second stimulation unit 12 is illustrated schematically in FIG. 13. Here, this is, for example, a cellular-phone-shaped stimulator, which can be carried in e.g. the shirt pocket or trouser pocket of the patient and which generates non-specific acoustic stimuli 22 by means of a loudspeaker 87.

Furthermore, provision can be made for an external programming instrument for the medical practitioner, by means of which instrument the parameters of the control unit 10, the generator unit 13 and/or the non-specific, physiological stimulation unit 12 can be set. Moreover, the patient can likewise be provided with an external programming instrument, by means of which the patient can switch off the stimulation equipment or can modify parameters of the stimulation units 11 and 12 within narrow limits set by the medical practitioner. Furthermore, the programming instrument intended for the patient can contain the functionality already explained above, by means of which the patient can independently, e.g. by actuating a button, switch into the first mode of operation, i.e. into the learning phase, from the second mode of operation if he/she feels that the therapy is insufficient, i.e. if e.g. the tremor or the hypokinesia are too pronounced. The programming instruments can communicate with the respective components of the stimulation instrument by means of radio links, for example.

The invention claimed is:
1. A device for desynchronizing a neuronal activity, the device comprising:
 a first stimulation unit configured to produce electrical first stimuli that suppress pathologically synchronous activity of neurons in at least one of a brain and a spinal cord of a patient;
 a second stimulation unit configured to produce second stimuli that are at least one of optical, acoustic, tactile and vibratory stimuli; and
 a control unit configured to control the first and the second stimulation units to produce the first and second stimuli in a first or a second mode of operation,
 wherein, in the first mode of operation, the control unit is configured to actuate the first and second stimulation units such that at least 60% of the second stimuli are produced during a time that the first stimuli are produced, and wherein, in the second mode of operation, the control unit is configured to actuate the first and second stimulation units such that at least 60% of the second stimuli are produced during a time that the first stimuli are not produced.

2. The device as claimed in claim 1, wherein in the first mode of operation, the control unit is configured to actuate the first and second stimulation units such that at least 80% of the second stimuli are produced during the time that the first stimuli are produced, and wherein, in the second mode of operation, the control unit is configured to actuate the first and second stimulation units such that at least 80% of the second stimuli are produced during the time that the first stimuli are not produced.

3. The device as claimed in claim 1, wherein the second stimuli applied on their own do not suppress the pathologically synchronous activity of the neurons.

4. The device as claimed in claim 1, wherein the patient can consciously perceive the second stimuli.

5. The device as claimed in claim 1, wherein the first stimulation unit comprises at least one electrode configured to deliver the first stimuli.

6. The device as claimed in claim 1, further comprising a measuring unit configured to record signals that reproduce the pathologically synchronous activity of the neurons.

7. The device as claimed in claim 6, wherein, in the second mode of operation, the control unit increases the number of first stimuli, the production of which is temporally coupled to the production of the second stimuli, if the measurement signals exceed a prescribed first threshold.

8. The device as claimed in claim 7, wherein the control unit is configured to switch into the first mode of operation from the second mode of operation if the measurement signals exceed a prescribed second threshold.

9. The device as claimed in claim 8, wherein the first threshold is smaller than the second threshold.

10. The device as claimed in claim 6, wherein the first stimulation unit produces the first stimuli using the measurement signals.

11. The device as claimed in claim 1, wherein the first stimuli are produced during a plurality of first time intervals and the second stimuli are produced during a plurality of second time intervals, and wherein at least 60% of the plurality of second time intervals overlap in time, respectively, with one of the plurality of first time intervals in the first mode of operation.

12. The device as claimed in claim 11, wherein the time overlap between one of the respective first time intervals and one of the respective second time intervals has a duration of at least 10% of the duration of the respective second time interval.

13. The device as claimed in claim 1, wherein the first stimuli are at least one or more sequences of electrical pulses.

14. The device as claimed in claim 1, wherein the first stimulation unit comprises a plurality of stimulation contact surfaces that are each configured to deliver the first stimuli to the at least one of the brain and the spinal cord of the patient, and wherein the first stimuli are embodied such that, if administered to a neuron population with an pathologically synchronous and oscillatory activity, the first stimuli reset the phase of the oscillatory activity of the neuron population.

15. The device as claimed in claim 1, further comprising a programming instrument configured to enable the patient to switch from the first mode of operation from the second mode of operation.

16. A device for desynchronizing a neuronal activity, the device comprising:

a first stimulation unit configured to produce electrical stimuli that suppress pathologically synchronous activity of neurons in at least one of a brain and a spinal cord of a patient;

a second stimulation unit configured to produce non-electrical stimuli that are at least one of optical, acoustic, tactile and vibratory stimuli, which can be consciously perceived by the patient; and a control unit configured to control the first and the second stimulation units to produce the electrical and non-electrical stimuli, respectively, wherein the control unit is configured to actuate the first and second stimulation units such that the electrical and non-electrical stimuli are administered at least partly at a same time to the patient during a learning phase to condition a nervous system of the patient, such that the nervous system reacts to the non-electrical stimuli without the electrical stimuli, and wherein the control unit is configured to actuate the first and second stimulation units such that the non-electrical stimuli are administered at least partly without the electrical stimuli to the patient during a stimulation phase that adjoins the learning phase.

17. A device for desynchronizing a neuronal activity, the device comprising:

a first stimulation unit configured to produce electrical stimuli that suppress pathologically synchronous activity of neurons in at least one of a brain and a spinal cord of a patient, wherein the electrical stimuli are produced during a plurality of first time intervals;

a second stimulation unit configured to produce non-electrical stimuli that are at least one of optical, acoustic, tactile and vibratory stimuli, wherein the non-electrical stimuli are produced during a plurality of second time intervals; and a control unit configured to control the first and the second stimulation units to produce the electrical and non-electrical stimuli in a first or a second mode of operation, wherein the control unit is configured to set the first and second time intervals such that at least 60% of the plurality of second time intervals each overlap in time with a respective one of the first time intervals in the first mode of operation and at least 60% of the plurality of second time intervals do not overlap with the plurality of first time intervals in the second mode of operation.

18. A method for desynchronizing a neuronal activity, the method comprising:

administering electrical first stimuli to at least one of a brain and a spinal cord of a patient, wherein the first stimuli suppress a pathologically synchronous activity of neurons in the at least one of the brain and the spinal cord; and administering second stimuli to the patient, wherein the second stimuli are at least one of optical, acoustic, tactile and vibratory stimuli, wherein, in a first mode of operation, at least 60% of the second stimuli are administered during a time that the first stimuli are administered, and, in a second mode of operation, at least 60% of the second stimuli are administered during a time that the first stimuli are not administered.

19. The method as claimed in claim 18, wherein, in the first mode of operation, at least 80% of the second stimuli are administered during the time that the first stimuli are administered, and, in the second mode of operation, at least 80% of the second stimuli are administered during the time that the first stimuli are not administered.

20. The method as claimed in claim 18, wherein the second stimuli administered on their own do not suppress the pathologically synchronous activity of the neurons.

21. The method as claimed in claim 18, wherein the second stimuli can be consciously perceived by the patient.

22. The method as claimed in claim 18, further comprising recording measurement signals that reproduce the pathologically synchronous activity of the neurons.

23. The method as claimed in claim 22, further comprising increasing the number of first stimuli in the second mode of operation if the measurement signals exceed a prescribed first threshold.

24. The method as claimed in claim 23, further comprising switching the second mode of operation to the first mode of operation if the measurement signals exceed a prescribed second threshold.

25. The method as claimed in claim 24, wherein the first threshold is smaller than the second threshold.

26. The method as claimed in claim 18, further comprising:
   administering the first stimuli during first time intervals; and
   administering the second stimuli during second time intervals,
   wherein at least 60% of the second time intervals overlap in time, respectively, with one of the first time intervals in the first mode of operation.

* * * * *